(12) United States Patent
Powell

(10) Patent No.: US 9,480,488 B2
(45) Date of Patent: Nov. 1, 2016

(54) SNAP-LOCK FOR DRILL SLEEVE

(71) Applicant: DePuy Synthes Products, Inc., Raynham, MA (US)

(72) Inventor: Sean Powell, Coatesville, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 85 days.

(21) Appl. No.: 14/613,139

(22) Filed: Feb. 3, 2015

(65) Prior Publication Data

US 2015/0150568 A1 Jun. 4, 2015

Related U.S. Application Data

(63) Continuation of application No. 11/410,846, filed on Apr. 24, 2006, now Pat. No. 8,974,466, which is a continuation of application No. 10/849,714, filed on May 19, 2004, now Pat. No. 7,033,363.

(51) Int. Cl.
*A61B 17/17* (2006.01)
*A61B 17/16* (2006.01)

(52) U.S. Cl.
CPC ....... *A61B 17/1725* (2013.01); *A61B 17/1615* (2013.01); *A61B 17/1728* (2013.01); *A61B 90/90* (2016.02); *A61B 90/94* (2016.02); *A61B 17/1735* (2013.01); *A61B 90/92* (2016.02); *A61B 2090/062* (2016.02); *A61B 2090/08021* (2016.02)

(58) Field of Classification Search
CPC .................. A61B 17/1725; A61B 17/1728
See application file for complete search history.

(56) References Cited

U.S. PATENT DOCUMENTS

| | | | |
|---|---|---|---|
| 1,685,785 A | 10/1928 | Muth | |
| 2,424,485 A | 7/1947 | Miller | |
| 3,108,500 A | 10/1963 | Merriman | |
| 3,765,034 A | 10/1973 | Johnston | |
| 3,892,232 A | 7/1975 | Neufeld | |
| 4,441,492 A | 4/1984 | Rydell et al. | |
| 4,522,201 A | 6/1985 | Tongue | |
| 4,549,538 A | 10/1985 | Schadrak, III et al. | |
| 4,708,540 A | 11/1987 | Heimbigner et al. | |

(Continued)

FOREIGN PATENT DOCUMENTS

| | | |
|---|---|---|
| DE | 3518496 A1 | 11/1986 |
| EP | 0550814 | 7/1993 |

(Continued)

*Primary Examiner* — David Bates
(74) *Attorney, Agent, or Firm* — Fay Kaplun & Marcin, LLP

(57) ABSTRACT

A device for drilling a hole in bone and for inserting bone screws into the drilled hole is provided. The device comprises a trocar, drill sleeve and protection sleeve in a telescopically nested configuration. The drill sleeve and protection sleeve may have an axial locking feature that allows the two pieces to be handled together as a unit by preventing inadvertent separation. The axial locking feature may comprise an integral annular ridge provided on one sleeve that cooperates with an annular groove provided on the other sleeve. One sleeve may also have at least one slot allowing the locking feature to be disengaged prior to separation of the sleeves. The sleeves may be easily separated with one hand by the user by the application of an axial separation force between a pair of flanges provided with the sleeves, and by a radial compression force applied to at least a portion of the drill sleeve.

16 Claims, 12 Drawing Sheets

(56) References Cited

U.S. PATENT DOCUMENTS

| | | |
|---|---|---|
| 4,740,117 A | 4/1988 | Schaff Deleury et al. |
| 4,862,883 A | 9/1989 | Freeland |
| 4,911,153 A | 3/1990 | Border |
| 4,936,170 A | 6/1990 | Zumeta |
| 4,969,781 A | 11/1990 | Fahrner et al. |
| 5,047,034 A | 9/1991 | Sohngen |
| 5,112,337 A | 5/1992 | Paulos et al. |
| 5,139,500 A | 8/1992 | Schwartz |
| 5,139,520 A | 8/1992 | Rosenberg |
| 5,152,765 A | 10/1992 | Ross et al. |
| 5,154,720 A | 10/1992 | Trott et al. |
| 5,163,940 A | 11/1992 | Bourque |
| 5,217,497 A | 6/1993 | Mehdian |
| 5,232,454 A | 8/1993 | Hollister |
| 5,403,322 A | 4/1995 | Herzenberg et al. |
| 5,423,824 A | 6/1995 | Akerfeldt et al. |
| 5,458,602 A | 10/1995 | Goble et al. |
| 5,474,561 A | 12/1995 | Yao |
| 5,478,341 A | 12/1995 | Cook et al. |
| 5,484,437 A | 1/1996 | Michelson |
| 5,575,794 A | 11/1996 | Walus et al. |
| 5,595,193 A | 1/1997 | Walus et al. |
| 5,601,550 A | 2/1997 | Esser |
| 5,613,971 A | 3/1997 | Lower et al. |
| 5,620,449 A | 4/1997 | Faccioli et al. |
| 5,720,748 A | 2/1998 | Kuslich et al. |
| 5,743,916 A | 4/1998 | Greenberg et al. |
| 5,755,721 A | 5/1998 | Hearn |
| 5,766,179 A | 6/1998 | Faccioli et al. |
| 5,797,909 A | 8/1998 | Michelson |
| 5,851,207 A | 12/1998 | Cesarone |
| 5,888,034 A | 3/1999 | Greenberg |
| 5,904,685 A | 5/1999 | Walawalkar |
| 5,947,971 A | 9/1999 | Kuslich et al. |
| 5,948,000 A | 9/1999 | Larsen et al. |
| 5,951,561 A | 9/1999 | Pepper et al. |
| 5,968,050 A | 10/1999 | Torrie |
| 6,019,767 A | 2/2000 | Howell |
| 6,027,506 A | 2/2000 | Faccioli et al. |
| 6,129,729 A | 10/2000 | Snyder |
| 6,176,823 B1 | 1/2001 | Foley et al. |
| 6,206,885 B1 | 3/2001 | Ghahremani et al. |
| 6,210,415 B1 | 4/2001 | Bester |
| 6,224,607 B1 | 5/2001 | Michelson |
| 6,254,604 B1 | 7/2001 | Howell |
| 6,254,605 B1 | 7/2001 | Howell |
| 6,270,498 B1 | 8/2001 | Michelson |
| 6,287,313 B1 | 9/2001 | Sasso |
| 6,325,393 B1 | 12/2001 | Chen et al. |
| 6,436,098 B1 | 8/2002 | Michelson |
| 6,443,956 B1 | 9/2002 | Ray |
| 6,451,023 B1 | 9/2002 | Salazar |
| 6,517,546 B2 | 2/2003 | Whittaker et al. |
| 6,562,046 B2 | 5/2003 | Sasso |
| 6,565,574 B2 | 5/2003 | Michelson |
| 6,575,974 B2 | 6/2003 | Gotfried |
| 6,575,981 B1 | 6/2003 | Boyd et al. |
| 6,595,995 B2 | 7/2003 | Zdeblick et al. |
| 6,629,976 B1 | 10/2003 | Gnos et al. |
| 6,635,062 B2 | 10/2003 | Ray, III et al. |
| 6,648,895 B2 | 11/2003 | Burkus et al. |
| 6,656,189 B1 | 12/2003 | Wilson et al. |
| 6,695,851 B2 | 2/2004 | Zdeblick et al. |
| 6,743,234 B2 | 6/2004 | Burkus et al. |
| 6,929,606 B2 | 8/2005 | Ritland |
| 7,033,363 B2 | 4/2006 | Powell |
| 2002/0091393 A1 | 7/2002 | Gundlapalli et al. |
| 2003/0028199 A1 | 2/2003 | Ghahremani et al. |
| 2003/0069581 A1 | 4/2003 | Stinson et al. |
| 2003/0130666 A1 | 7/2003 | Whittaker et al. |
| 2003/0135211 A1 | 7/2003 | Cho |
| 2003/0195517 A1 | 10/2003 | Michelson |
| 2003/0195519 A1 | 10/2003 | Zdeblick et al. |
| 2003/0204262 A1 | 10/2003 | Ferguson et al. |

FOREIGN PATENT DOCUMENTS

| | | |
|---|---|---|
| EP | 1092395 A2 | 4/2001 |
| EP | 1356777 | 10/2003 |
| WO | 03020137 A1 | 3/2003 |

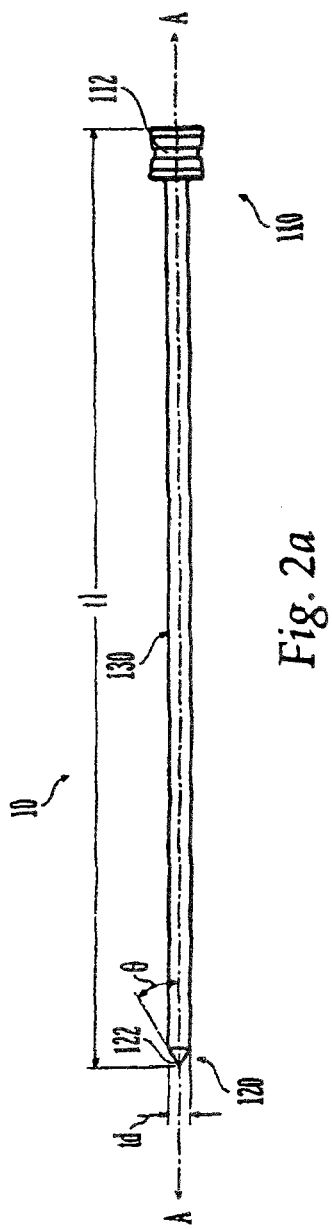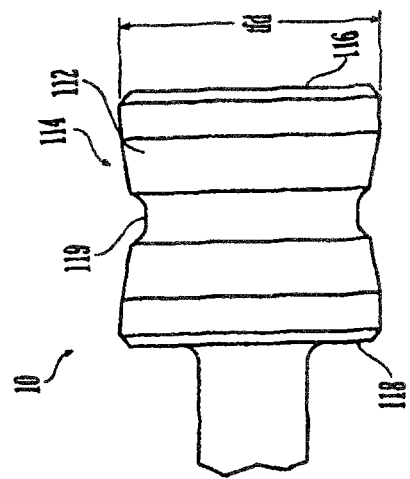
Fig. 2a
Fig. 2b

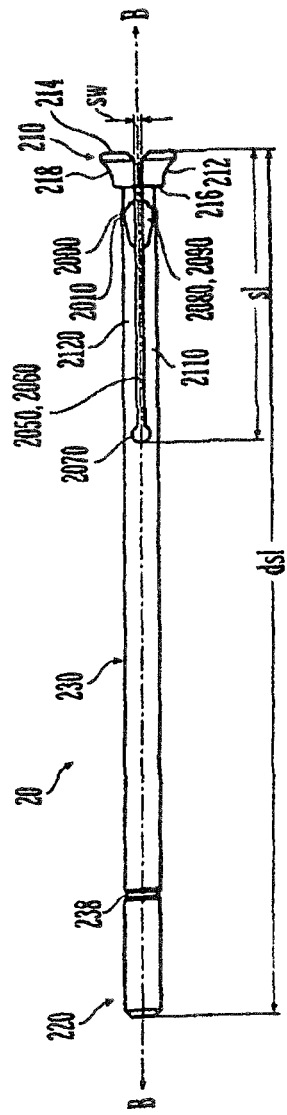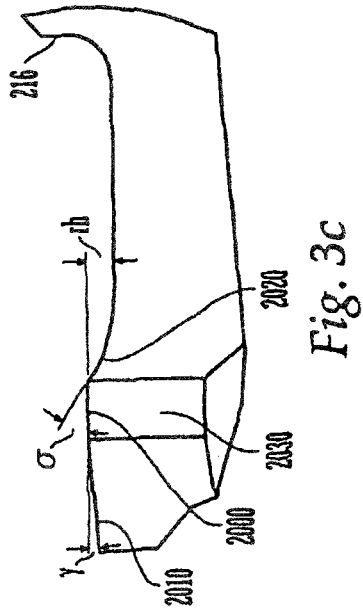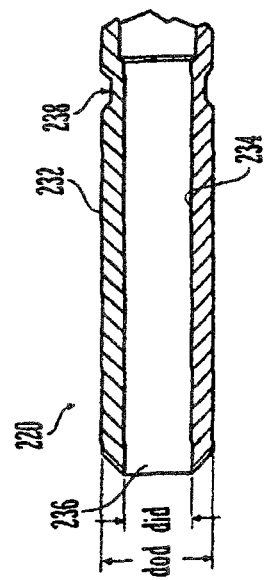

SNAP-LOCK FOR DRILL SLEEVE

CROSS-REFERENCE TO RELATED APPLICATION

The present application is a Continuation Application of U.S. patent application Ser. No. 11/410,846 filed on Apr. 24, 2006, now U.S. Pat. No. 8,974,466; which is a Continuation of U.S. patent application Ser. No. 10/849,714 filed on May 19, 2004, now U.S. Pat. No. 7,033,363. The disclosures of the above applications/patents are incorporated herein by reference.

FIELD OF THE INVENTION

The present invention is related to a drill sleeve system. More particularly, the invention is related to a snap lock design for provisionally retaining a drill sleeve to a screw insertion sleeve.

BACKGROUND OF THE INVENTION

Orthopedic fixation devices such as plates are frequently coupled to bone with fasteners inserted through holes in the device. For fractures of the long bones such as the humerus or the femur, fractures may be treated by inserting an elongated member into a channel reamed in the intramedullary canal. This elongated member, or "intramedullary nail" as it is known in the art, may provide stability to the bone until the fractured bone segments heal together. Intramedullary nails may be fastened to the bone in which they reside using screws inserted through pre-formed holes in the nail. Corresponding holes may be drilled in the adjacent bone to allow easier insertion of the screws in the bone. These holes can be formed with the aid of a drill guide aligned with the targeted screw hole. A drill may be introduced through the drill guide is thus guided through the screw hole to drill a hole in the bone underlying the screw hole.

In an effort to reduce the total number and length of incisions created when installing the intramedullary nail and inserting the securing fasteners, the drilling and screw insertion process can be performed percutaneously. Thus, an incision may be made in the skin overlying the bone, and a trocar may be inserted into the incision and used to separate the soft tissue to create an initial passage down to the bone. A drill may be inserted through the drill sleeve and used to form a hole in the bone as previously described. A screw insertion sleeve may thereafter be inserted through the passage and used to facilitate engagement of the screw with the screw hole and bone. Advantageously, these three pieces (trocar, drill sleeve, screw insertion sleeve) may be provided as a single unit to facilitate handling and use by the surgeon. Thus, the three pieces may be nested within each other and inserted as a single unit.

To further facilitate use of these three-piece units, at least two of the pieces may be provided with features aimed at preventing separation of the individual pieces while they are being handled by the user. For example, snap rings, ball detents, or threads may be used to secure the pieces together. To remove one piece from the other (e.g. to remove the drill sleeve from the screw-insertion sleeve), the user may pull the pieces apart (in the case of a snap-ring or ball-detent) or may unthread the pieces (where threaded pieces are provided).

Snap-ring locking devices may be difficult to sterilize, and threaded pieces may be difficult to handle in the surgical environment. Thus there exists a need for a multiple piece drill sleeve system having a simple, easy to sterilize design for provisionally retaining at least two pieces of the system with respect to each other, and which allows easy separation of those pieces when desired by the user.

SUMMARY OF THE INVENTION

An orthopedic system is disclosed comprising a first sleeve member having an outer surface and an inner surface defining a longitudinal bore and a surface; and a second sleeve member having an outer surface and an inner surface defining a longitudinal bore, where the second sleeve member may further be configured to be at least partly received within the bore of the first sleeve member. The longitudinal bore of one of the first and second sleeves may be configured to receive a drill bit therethrough to drill a hole in bone. Further, one of the first and second sleeve members may further comprise a protrusion and the other may comprise a corresponding recess, the protrusion and recess being co-operable to provisionally axially lock the first and second sleeve members together when the second sleeve member is at least partly received within the bore of the first sleeve member. The second sleeve may be dis-engageable from the first sleeve through the application of an axial separation force between the first and second sleeves and a radial compression force to at least a portion of the second sleeve.

The system may also comprising a trocar configured to be received within the longitudinal bore of the second sleeve. The first and second sleeve members further may each have a proximal end comprising a flange member and a distal end comprising a tapered tip region. The longitudinal bore of the first sleeve may further be configured to receive a driver and bone fastener therethrough to allow insertion of the fastener into bone in a direction along the longitudinal axis of the bore. Moreover, the tapered tip of at least one of the first or second sleeve members configured to align with a fastener hole in a bone fixation element. The bone fixation element may be a bone plate or an intramedullary nail.

The protrusion may be integrally formed with the associated sleeve, and in one embodiment may comprise at least one circumferential ridge. The recess may comprise at least one circumferential groove corresponding to the at least one ridge. The protrusion further may comprise first and second tapered surfaces.

The second sleeve may comprise at least one longitudinal slot disposed between the inner and outer surfaces of the sleeve, the slot running from at least one end of the sleeve and having a length, the slot further configured to render at least a portion of the sleeve radially flexible.

The at least one slot may divide a first end of the sleeve into first and second halves, wherein pressing the first and second halves toward each other may disengage the ridge from the recess, thereby allowing the first and second sleeves to be axially engaged with, or disengaged from, each other.

The second sleeve may have two longitudinal slots diametrically disposed with respect to each other about the circumference of the sleeve. The protrusion may comprise at least one tapered surface configured to facilitate radial compression of the second sleeve when the sleeve is inserted into the bore of the first sleeve.

The first and second sleeves and the trocar may be color coded to provide a visual indication of the size of a bone screw that can be received through the bore of the first sleeve.

The outer surface of the first sleeve may be configured to be received within the bore of an aiming arm of an intramedullary nail to align the sleeve with a targeted fastener hole in a portion of the intramedullary nail.

An orthopedic system is provided comprising a first sleeve having proximal and distal ends, a longitudinal axis and inner and outer surfaces.

A second sleeve may be provided having proximal and distal ends, a longitudinal axis, and inner and outer surfaces, where the inner surface is configured to receive at least a portion of the first sleeve. The inner surface may further be configured to receive a bone fastener and driver for inserting the fastener into the hole drilled in bone. The inner surface of at least one of the first and second sleeves may be configured to receive a drill bit for drilling a hole in bone. At least a portion of the first sleeve may be slidably receivable within at least a portion of the second sleeve.

One of the second sleeve inner surface and the first sleeve outer surface may comprise a projection, and the other may comprise a corresponding recess so that when the first sleeve is received within the second sleeve, the projection and recess may cooperate to releasably axially engage the first sleeve with the second sleeve.

The projection may be integrally formed with the associated sleeve. The protrusion may also comprise at least one circumferential ridge, or a plurality of discrete protruding elements. The recess may comprise at least one circumferential groove corresponding to the at least one ridge. The protrusion may comprise first and second tapered surfaces configured to engage a portion of the inner surface of the second sleeve.

The sleeves may be disengageable from each other by applying an axial separation force between the first and second sleeves and a radial compression force to at least a portion of the first sleeve.

The system may further comprise a trocar configured to be received within the longitudinal bore of the first sleeve. The sleeves further may each have a proximal end comprising a flange member and a distal end comprising a tapered tip region. The tapered tip of at least one of the first or second sleeves may be configured to align with a fastener hole in a bone fixation element. The bone fixation element may be a bone plate or an intramedullary nail.

The first sleeve may comprise at least one longitudinal slot disposed between the inner and outer surfaces of the sleeve, the slot running from at least one end of the sleeve and having a length, the slot further configured to render at least a portion of the sleeve radially flexible. The at least one slot may divide a first end of the first sleeve into first and second halves, wherein when the first sleeve is fully received within the second sleeve, pressing the first and second halves toward each other disengages the ridge from the recess, thereby allowing the first sleeve to be removed from the second sleeve.

When the first sleeve is inserted into the second sleeve, the first tapered surface may cooperate with the inner surface of the second sleeve to radially compress the first and second halves together. The first sleeve may have two longitudinal slots diametrically disposed with respect to each other about the circumference of the sleeve. The protrusion may comprise at least one tapered surface configured to facilitate radial compression of the first sleeve when the sleeve is inserted into the bore of the second sleeve.

The first and second sleeves and the trocar may be color coded to provide a visual indication of the size of a bone screw that can be received through the bore of the first sleeve.

Moreover, the outer surface of the first sleeve may be configured to be received within the bore of an aiming arm of an intramedullary nail to align the sleeve with a targeted fastener hole in a portion of the intramedullary nail.

A method of drilling a hole in bone is provided, comprising: (a) providing a drill sleeve and protection sleeve combination, the drill sleeve telescopically receivable within at least a portion of the protection sleeve, the drill sleeve having an inner surface for receiving a drill bit for drilling a hole in a bone, the drill sleeve having an outer surface comprising one of a projection and a recess configured to engage a corresponding recess or projection disposed on an inner surface of the protection sleeve to provisionally axially lock the sleeves together; wherein the drill and protection sleeve are separable from each other through the application of an axial separation force between the sleeves and a radial compression force to at least a portion of the drill sleeve; (b) advancing the drill sleeve and protection sleeve combination through an incision in a patient; (c) advancing the drill sleeve and protection sleeve to align with a bone fixation element overlying a portion of the bone; (d) inserting a drill bit through the drill sleeve and advancing the drill bit to engage bone; (e) rotating the drill to produce a hole in the bone; (f) removing the drill bit from the drill sleeve; and (g) applying an axial separation force between the drill sleeve and the protection sleeve and applying a radial compression force to a portion of the drill sleeve to disengage the two.

The drill sleeve and protection sleeve further may comprise a trocar configured to be received within the longitudinal bore of the drill sleeve. The sleeves further each have a proximal end comprising a flange member and a distal end comprising a tapered tip region. The bone fixation element may be a bone plate or an intramedullary nail. The projection may be integrally formed with the associated sleeve. The projection may comprise a plurality of discrete protruding elements. The projection may comprise at least one circumferential ridge. The recess may comprise at least one circumferential groove corresponding to the at least one ridge. The protrusion may comprise first and second tapered surfaces configured to engage a portion of the recess.

The drill sleeve may comprise at least one longitudinal slot disposed between the inner and outer surfaces of the sleeve, the slot running from at least one end of the sleeve and having a length, the slot further configured to render at least a portion of the sleeve radially flexible. the at least one slot may divide a first end of the drill sleeve into first and second halves so that when the drill sleeve is fully received within the screw insertion sleeve, pressing the first and second halves toward each other may disengage the protrusion from the recess, thereby allowing the drill sleeve to be removed from the screw insertion sleeve.

The method may comprise the additional steps of: (g) inserting a bone fastener and screwdriver through the protections sleeve; and (h) driving the bone fastener into the hole in the bone to fix the bone fixation element to the bone.

The method may further comprising the step, between steps (a) and (b), of: inserting the outer surface of the protection sleeve into a bore in an aiming arm attached to an intramedullary nail; step (c) may further comprise advancing the protection sleeve and drill sleeve through the bore in the aiming arm to align with a fastener hole in the bone fixation element; and step (e) comprises drilling a hole in the bone through the fastener hole in the intramedullary nail.

The method may further comprising the steps of: (h) inserting a bone fastener and screwdriver through the protection sleeve; (i) driving the bone fastener into the hole in the bone to fix the bone fixation element to the bone; and (j) removing the protection sleeve from the patient.

BRIEF DESCRIPTION OF THE DRAWINGS

Preferred features of the present invention are disclosed in the accompanying drawings, wherein similar reference characters denote similar elements throughout the several views, and wherein:

FIGS. 2a and 2b are side and detail views of the trocar element of the device of FIG. 1;

FIGS. 3a through 3e are side, top, partial detail and detail views, respectively, of the drill sleeve of the device of FIG. 1;

DETAILED DESCRIPTION OF THE PREFERRED EMBODIMENTS

Figure 1:
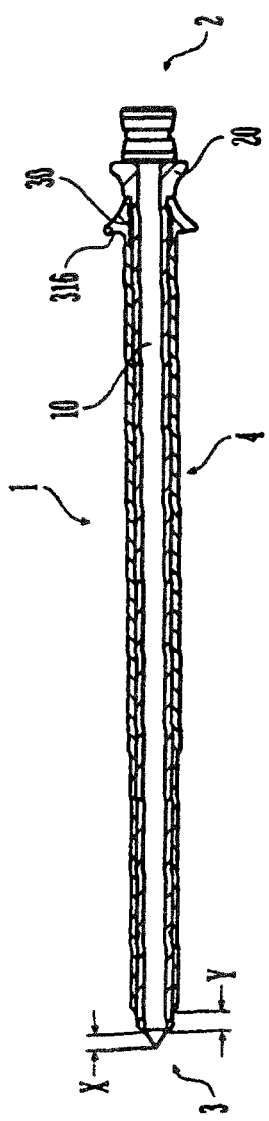
FIG. 1 is a cross sectional assembled view of a protection sleeve, drill sleeve and trocar device of the present invention.

A drilling and screw insertion sleeve device is disclosed for use in installing fasteners for securing orthopedic fixation devices, such as bone plates, intramedullary nails, and the like, to bone segments of the human anatomy. Such fixation devices may be used to repair fractured bones or may be installed to protect against the fracturing of weak bones. FIG. 1 shows an exemplary device 1 for such use, comprising a trocar 10, a drill sleeve 20 and a protection sleeve 30. As illustrated, the trocar 10, drill sleeve 20 and protection sleeve 30 are in a nested configuration which allows them to be introduced through a surgical incision as a single unit. Thus, when the device 1 is used for drilling holes and placing screws in bone, the device 1 may be inserted through a single incision made through the patient's skin immediately overlying one or more bone screw holes of a plate, nail, etc. The individual elements of the system may then be removed as necessary to perform the desired procedure. For example, the trocar 10 may be removed after the device 1 has been appropriately placed in contact with the patient's bone or the screw hole of a fixation device.

As shown in FIG. 1, the device 1 has a proximal user end 2, a distal incision end 3, and a generally cylindrical longitudinal central portion 4 generally formed by the outer surface of the protection sleeve 30. The proximal end 2 is configured for easy grasping by the user, and the distal end 3 may have a tapered configuration to facilitate insertion into an incision in the patient.

Referring to FIGS. 2a and 2b, the trocar 10 comprises a rod-like member having proximal and distal ends 110, 120 and a cylindrical center portion 130 having an outer diameter "td," a longitudinal axis "A-A," and a length "U." The proximal end 110 may comprise a flange element 112 having an increased diameter "tfd," and an outer gripping surface 114 configured to be easily grasped by a user. The flange element 112 may further comprise a proximal end face 116 and a distal face 118. The proximal end face 116 may be configured to receive a user input force, such as may be applied by the thumb or palm of the hand, while the distal face 118 may be configured to engage a proximal face 214 of the drill sleeve flange 212 to transmit the applied user input force thereto.

The trocar flange element 112 may have one or more annular grooves 119 that have a band of color applied to distinguish the trocar as being of a particular size. That is, since the inventive system may be provided in any of a variety of sizes, it may be advantageous to provide a simple color-coding of the device elements to provide a clear visual indication to the user of the system size. Thus, groove 119 may be provided with a band of color that matches similar color bands provided on the drill sleeve 20, protection sleeve 30, and drill 40 of the same system size. Color may be applied to the groove 119 by painting or other appropriate technique.

The trocar distal end 120 may be tapered to allow easier insertion into the incision in the patient. The taper may form an angle θ with respect to the longitudinal axis "A-A," which in the illustrated embodiment is about 30°, although other angles may be provided. The distal end 120 may have a tip portion 122 forming a sharp point to further facilitate movement of the trocar 10 (as well as drill sleeve 20 and protection sleeve 30) 1 through the surrounding tissue. In use, the tip portion 122 may be used to separate the soft tissue as it is being pressed into and through the incision.

Referring to FIGS. 3a through 3e, an exemplary drill sleeve 20 is shown having proximal and distal ends, 210, 220, a central cylindrical portion 230 having a longitudinal axis "B-B", and a length "dsl." The drill sleeve 20 further may have an outer cylindrical surface 232 having a diameter "dod," and an inner cylindrical surface 234 having a diameter "did" defining a longitudinal bore 236 running along the length "dsl."

The drill sleeve bore 236 may be sized to accept the cylindrical center portion 130 of trocar 10 during insertion of the sleeve 20 into the patient as part of system 1, and as illustrated in FIG. 1. The bore 236 may also be sized to accept an appropriately sized drill bit 40 (FIGS. 7, 9) to allow drilling of underlying bone through the drill sleeve 20 along longitudinal axis "B-B" once the sleeve 20 has been introduced through the incision.

The proximal end 210 of the drill sleeve 20 may comprise a flange 212 having a diameter "dsfd" that is greater than the sleeve outer diameter "dod." The flange 212 may further have a proximal end face 214 configured to engage the distal end face 118 of the trocar 10 when the trocar is fully inserted into the drill sleeve 20 (see FIG. 1). The flange 212 may further have a distal end face 216 configured to engage a proximal annular end face 314 of the protection sleeve 30 (see FIGS. 1 and 4b), as will be described in more detail later.

As shown in FIG. 3a, to facilitate insertion of the trocar 10 within the drill sleeve 20, bore 236 may taper slightly outward at a point immediately adjacent the sleeve proximal end 210.

The drill sleeve flange 212 may have an outer gripping surface 218 configured to allow easy grasping by a user. In the illustrated embodiment, the outer diameter of the proximal end face 214 is larger than the outer diameter of distal end face 216, such that gripping surface 218 disposed therebetween is angled to face slightly in the distal direction. Gripping surface 218 is also slightly concave to more closely conform to the user's fingers as they may be applied to pull the drill sleeve 20 out of engagement with protection sleeve 30.

The drill sleeve distal end 220 may be tapered to allow easier insertion into the incision in the patient. The taper may form an angle α with respect to the longitudinal axis "B-B," which in the illustrated embodiment is about 30°, and which substantially matches angle θ of the trocar distal end 120. The length "dsl" may be such that when the trocar 10 is inserted through the bore 236 of the drill sleeve, the distal tip 122 extends a distance "x" distally beyond the distal end 220 of the drill sleeve 20 (see FIG. 1). This distance "x" may be selected so that the tapered ends 122, 220 of the trocar 10 and drill sleeve 20 correspond to form one relatively smooth tapered surface which may facilitate the insertion and advancement of the two pieces into a patient incision.

The drill sleeve 20 may further incorporate a locking feature to provisionally axially retain the drill sleeve within the protection sleeve 30 during handling and installation. This locking feature may be easily overcome by the application of finger pressure between the drill and protection sleeve flanges 212, 312 (FIG. 4a), as previously noted. In the embodiment illustrated in FIGS. 3a & 3c, the locking feature comprises a circumferential ridge 2000 located adjacent proximal end flange 212. As illustrated in FIG. 3c, ridge 2000 may have first and second tapered surfaces 2010, 2020 and a top surface 2030 having a height "rh". The first and second tapered surfaces 2010, 2020 may be oriented at taper angles γ, σ with respect to the longitudinal axis "B-B" of the drill sleeve 20. The tapers 2010, 2020 may allow smooth engagement and disengagement of the circumferential ridge with an internal recess 3000 (FIG. 4c) of the protection sleeve 30, as will be described in more detail later. To further facilitate engagement/disengagement, one or both of the tapered surfaces may also be slightly concave. Thus, when the drill sleeve 20 is inserted into the protection sleeve 30, the first tapered surface 2010 may engage the inner surface 334 of the protection sleeve 30 to provide a smooth compression of the proximal end 210 of the drill sleeve 20. Once the ridge 2000 is fully engaged with the recess 3000, the second tapered surface 2020 may contact the proximal end wall 3010 of the recess 3000 in the protection sleeve 30 to prevent the drill sleeve 20 from falling out of the proximal end 210 of the protection sleeve 30 during normal handling.

In one embodiment (FIG. 3c), the second surface taper angle α may be greater than the first surface taper angle γ to result in a relatively low required engagement force between the pieces 20, 30 and a slightly higher disengagement force for separation of the pieces. It is noted that although the ridge 3000 is illustrated as having unequal first and second taper angles γ, σ, the drill sleeve 20 could be provided with equal taper angles (see FIG. 5b).

γ may be from about 5 degrees to about 90 degrees, and in one embodiment, γ is about 30 degrees. σ may be from about 1 degree to about 90 degrees, and in one embodiment, σ is about 5 degrees. Ridge height "rh" may be from about 0.2 mm to about 1.0 mm, and in one embodiment is about 0.4 mm.

As shown in FIG. 3a, a pair of longitudinal slots 2050, 2060 may be provided in diametrically opposed relationship in the drill sleeve proximal end 210 to allow compression of the drill sleeve 20 so that the circumferential ridge 2000 may engage the protection sleeve recess 3000. Thus, the slots 2050 may divide the proximal end 210 of the drill sleeve into first and second opposing halves 2110, 2120 that may be flexed toward each other to temporarily reduce the outer dimension of the circumferential ridge 2000 during installation and removal of the drill sleeve 20 from the protection sleeve 30.

As shown in FIG. 3a, the slots 2050, 2060 may run from the drill sleeve proximal end 210 to a location between the sleeve proximal and distal ends 210, 220. The slots 2050, 2060 may have a length "sl" and a width "sw," and at their distal ends may be provided with a stress-reducing enlarged cutout 2070, which in the illustrated embodiment is a circular cutout. Slot length "sl" may be from about 20 mm to about 150 mm, and in one embodiment is about 65 mm. Slot width "sw" may be from about 0.5 mm to about 3.0 mm, and in one embodiment is about 1.0 mm.

It is noted that while the drill sleeve of FIG. 3a has been described as having a pair of slots 2050, 2060, drill sleeve 20 could be provided with one or more slots, as desired. Further, where more than one slot is employed, the slots may have different lengths and/or different widths. Furthermore, the slots may have varying widths along their respective lengths.

Figure 3D:
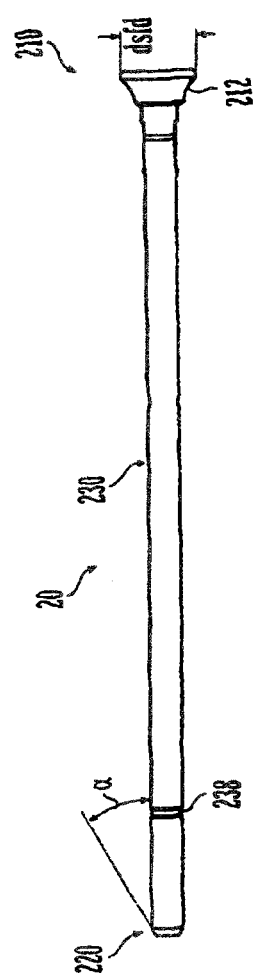
Figure 3E:
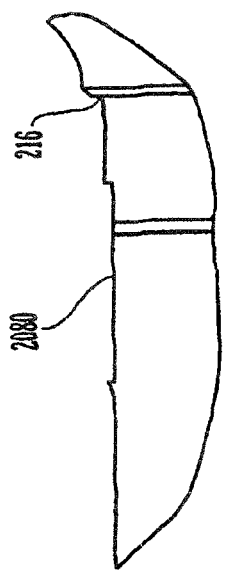

As shown in FIGS. 3a and 3e, side flats 2080, 2090 may be provided on the outer surface 232 of the drill sleeve adjacent the drill sleeve proximal end 210. These flats 2080, 2090 may be disposed at 180 degree intervals, and may be centered on the slots 2050, 2060 to further facilitate insertion of the drill sleeve 20 into the protection sleeve 20. Since the slots 2050, 2060 only allow compression of the drill sleeve 20 in one dimension, the flats 2080, 2090 eliminate the remaining interference between the circumferential ridge 2000 and the inner surface 334 of the protection sleeve 30 adjacent to the slots 2050, 2060. It is noted that providing the drill sleeve 20 with more than two slots may allow the sleeve to be compressed in two dimensions, and thus the side flats 2080, 2090 may not be required.

As with the trocar 10, the drill sleeve 20 may be color-coded to distinguish the sleeve as corresponding to a particularly sized drill bit. Thus, the central cylindrical portion 230 may have an annular groove 238 formed in the outer surface 232 into which a band of color may be applied. The color applied may match the color applied to a trocar 10 that is sized to be received within the bore 236 of the drill sleeve 20.

Figure 4A:
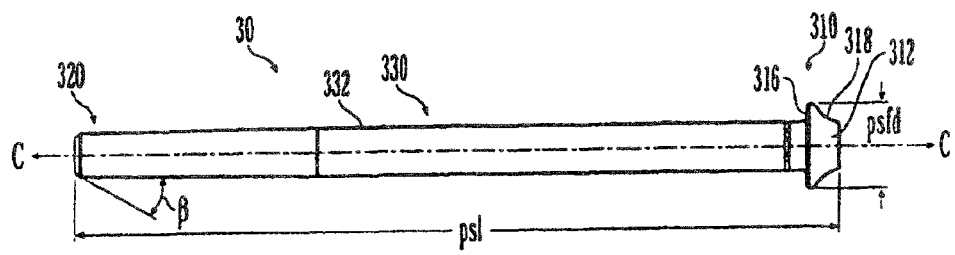
FIGS. 4a, 4b and 4c are side, cross-section and detail cross-section views, respectively, of the protection sleeve of the device of FIG. 1.
Figure 4B:
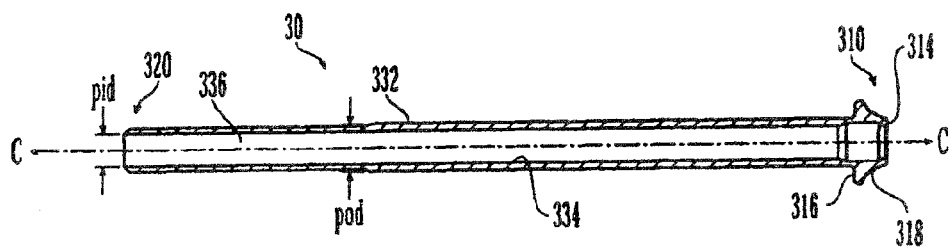
Figure 4C:
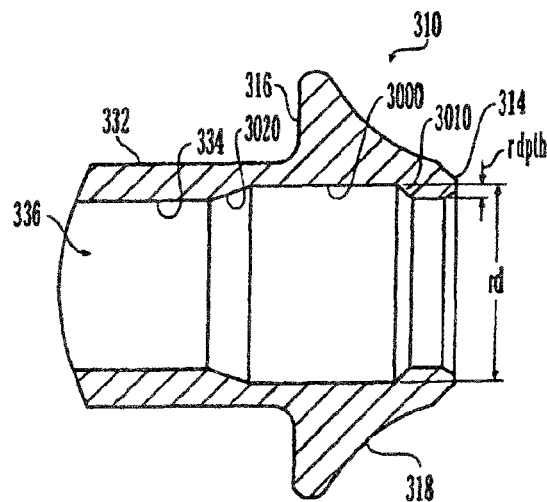

Referring to FIGS. 4a through 4c, an exemplary protection sleeve 30 is shown having proximal and distal ends, 310, 320, a central cylindrical portion 330 having a longitudinal axis "C-C", and a length "psl." The protection sleeve 30 further may have an outer cylindrical surface 332 having a diameter "pod," and an inner cylindrical surface 334 having a diameter "pid" defining a longitudinal bore 336 running along the length "psl."

Figure 10:
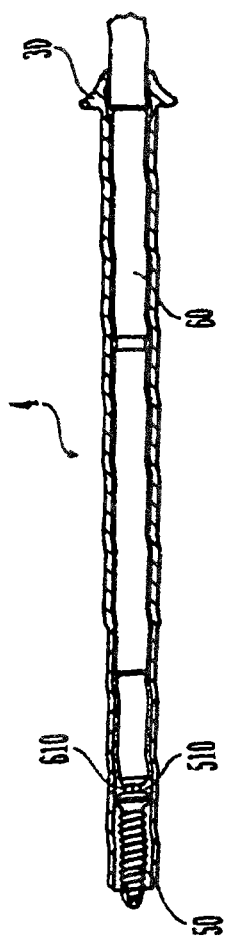
FIG. 10 is a cross-section view of the system of FIG. 1 without the trocar and drill sleeve, and with a screw and screwdriver inserted through the protection sleeve.

The protection sleeve bore 336 may be sized to accept the cylindrical center portion 230 of drill sleeve 20 during insertion of the sleeves 20, 30 into the patient as part of system 1, and as illustrated in FIG. 1. The bore 336 may also be sized to accept an appropriately sized screw 50 and screwdriver 60 (FIG. 10) to facilitate insertion of the screw into the underlying bone through the protection sleeve 30 along the sleeve longitudinal axis "C-C" once the sleeve 30 has been introduced through the incision. Thus, the inner diameter "pid" may be about 1.0 mm to about 17.0 mm to allow insertion of screws, spiral blades or helical blades therethrough. Further description regarding such blades is provided in co-pending U.S. nonprovisional patent application Ser. No. 10/269,976 to Roth et al., filed Oct. 15, 2002 and titled "Orthopedic Implant Insertion Instruments," the entirety of which application is incorporated herein by reference. Specifically, the protection sleeve 30 may receive screws having major diameters of from about 1 mm to about 8 mm and having head diameters of about 1.0 mm to about 12.0 mm.

The proximal end 310 of the protection sleeve 30 may comprise a flange 312 having a diameter "psfd" that is greater than the sleeve outer diameter "pod." The flange 312 may further have a proximal end face 314 configured to engage the distal end face 216 of the drill sleeve 20 when the drill sleeve is fully inserted into the protection sleeve 30 (see FIG. 1). The flange 312 may further have a distal end face 316 configured to allow gripping by a user.

The protection sleeve flange 312 may further have an outer gripping surface 318 disposed between the proximal and distal end faces 314, 316 and configured to allow easy grasping by a user. In the illustrated embodiment, the outer diameter of the proximal end face 314 is smaller than the outer diameter of distal end face 316, such that gripping surface 318 disposed therebetween is angled to face slightly in the proximal direction. Gripping surface 318 also may be slightly concave to more closely conform to the user's fingers as they may be applied to hold the protection sleeve 30 while pulling the drill sleeve 20 out of engagement with protection sleeve 30.

As shown in FIGS. 4b and 4c, and previously described in relation to the circumferential ridge 2000 of drill sleeve 20, the protection sleeve 30 may further have a recess 3000 disposed in the bore 336 adjacent the sleeve proximal end 310. This recess 3000 may be configured to engage the circumferential ridge 2000 of the drill sleeve 20 when the drill sleeve is fully inserted into the protection sleeve 30. The recess 3000 may have a diameter "rd," and proximal and distal end surfaces 3010, 3020 that provide a transition between the recess 3000 and the bore 336. Recess diameter may be sized to provide a recess depth "rdpth" of from about 0.2 mm to about 1.0 mm to provide the desired interference and locking with circumferential ridge 2000. In one embodiment, the recess depth "rdpth" is about 0.6 mm. Further, to facilitate insertion of the drill sleeve 20 into the protection sleeve 30, the bore 336 may taper slightly outward immediately adjacent the sleeve proximal end 310.

The protection sleeve distal end 320 may be tapered to allow easier insertion into the incision in the patient. The taper may form an angle β with respect to the longitudinal axis "C-C," which in the illustrated embodiment is about 30°, and which substantially matches angles θ and α of the trocar and drill sleeve distal ends 120, 220. Further, the length "psl" may be such that when the drill sleeve 20 is inserted through the bore 336 of the protection sleeve, the distal end 220 extends a distance "y" distally beyond the distal end 320 of the protection sleeve 30 (see FIG. 1). This distance "y" may be selected so that the tapered ends 122, 220, 320 of the trocar 10, drill sleeve 20 and protection sleeve correspond to form one relatively smooth tapered surface which may facilitate the insertion and advancement of the two pieces into a patient incision.

Figure 5C:
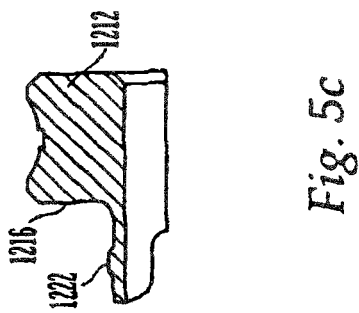
FIGS. 5a, 5b and 5c are side and cross-section views of the drill sleeve of FIG. 3a employing an alternative retention feature design.
Figure 5A:
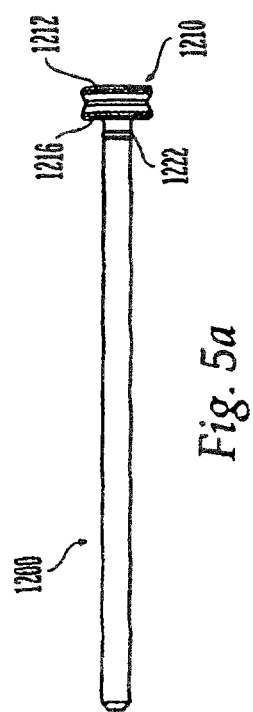
Figure 5B:
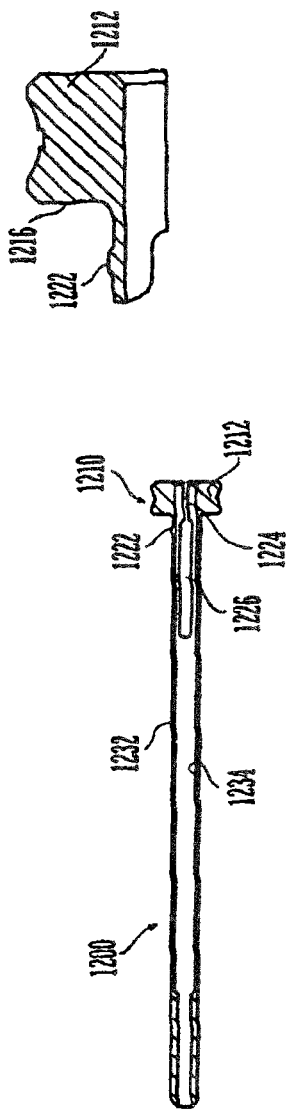
Figure 6A:
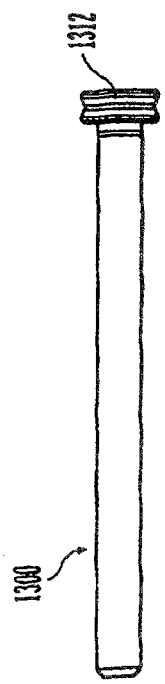
FIGS. 6a, 6b and 6c are side and cross-section views of the protection sleeve of FIG. 4a for use with the drill sleeve retention feature design of FIGS. 5a, 5b and 5c.
Figure 6B:
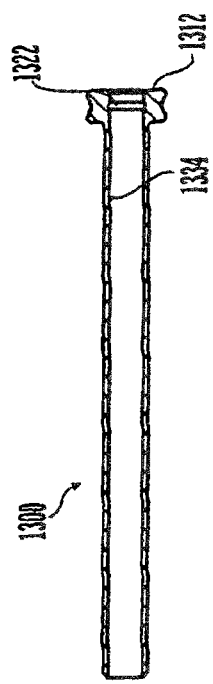

FIGS. 5a-5c show a drill sleeve 1200 having an alternative provisional retention feature comprising a raised circumferential ridge 1222 configured to engage a corresponding recess 1322 in an alternative protection sleeve 1300 (see FIGS. 6a, 6b). The ridge 1222 may be disposed on the outer surface 1232 of the sleeve 1200 adjacent the distal end face 1216 of flange 1212. As shown in FIGS. 5a-5c the drill sleeve 1200 may have a longitudinal slot 1224 formed in the proximal end 1210 and extending distally to intersect with an elongated window 1226 disposed between the outer and inner surfaces 1232, 1234 of the sleeve. This combination of slot 1224 and window 1226 provides the desired flexibility to the proximal end 1210 of the drill sleeve 1200 to allow it to be compressed so that the drill sleeve 20 can be received within the protection sleeve 30 as described previously in relation to the drill sleeve 20 of FIG. 3a.

Figure 6C:
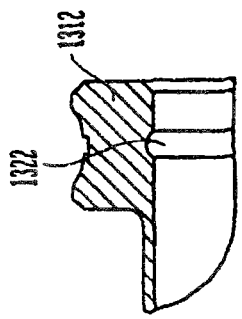

FIGS. 6a-6c show a protection sleeve 1300 for use with the drill sleeve 1200 of FIGS. 5a-5c in which circumferential recess 1322 is disposed in inner surface 1334 adjacent proximal end flange 1312. Recess 1322 may be configured to receive ridge 1222 of the drill sleeve 1200 when the drill sleeve is inserted fully into the protection sleeve 1300 as described previously in relation to the drill sleeve 20 and protection sleeve 30 of FIGS. 3a and 4a.

Furthermore, it should be noted that the drill sleeve 1200 of FIGS. 5a-5c and the protection sleeve 1300 of FIGS. 6a-6c may further incorporate any or all of the other features previously described in relation to the drill sleeve 20 and protection sleeve 30 of FIGS. 3a and 4a (e.g. distal end taper, dimensions, color-coding, flange configurations, etc).

It should also be noted that although the invention has been described as having the projection formed on the drill sleeve and the recess formed in the protection sleeve, this arrangement may be reversed. Thus, a projection or projections may be provided on the inner surface of the protection sleeve and the corresponding recess or recesses may be provided on the drill sleeve outer surface.

Furthermore, the projection provided on the drill sleeve (or alternatively on the protection sleeve) may be formed by machining. Thus, if the sleeve itself is machined from a single piece of material, the projection may be formed during the general machining process. Alternatively, the projection may be provided by depositing a weld bead or fillet about the circumference of the drill sleeve/protection sleeve and then machining or grinding the bead or filled to the desired shape. Further, the projection may comprise a series of raised rivets or applied nubs integrated into the surface of the drill guide/protection sleeve and configured to engage the recess of the protection sleeve.

In yet another alternative embodiment, the projection could be formed using a short sleeve or annular ring applied to the drill sleeve or protection sleeve. Such an arrangement may simplify the machining of the drill sleeve/protection sleeve, since instead of being machined-in, the ring could be fixed in place using an appropriate means, including welding, brazing, bonding, shrink fit or press fit to the associated sleeve.

Figure 7:
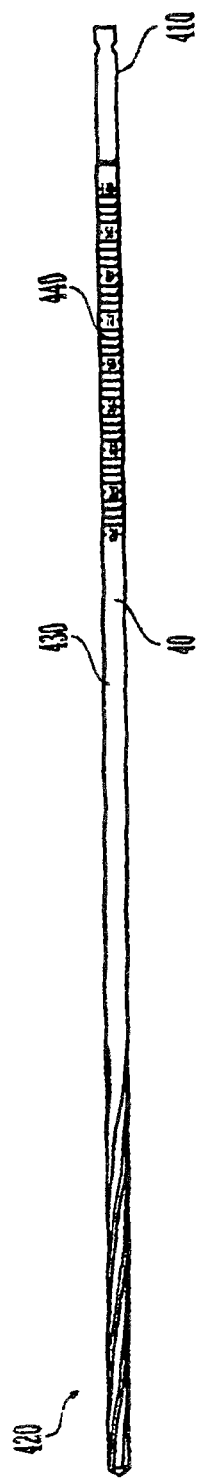
FIG. 7 is a side view of an exemplary drill bit for use with the device of FIG. 1.
Figure 9:
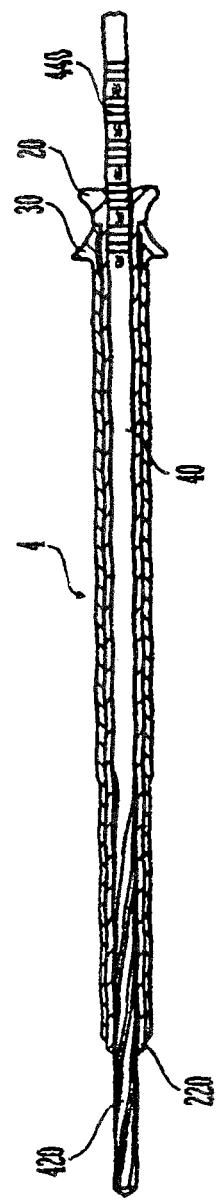
FIG. 9 is a cross-section view of the device of FIG. 1 without the trocar, and with the drill bit of FIG. 7 inserted through the drill sleeve.

FIG. 7 shows an exemplary drill bit 40 for use with the device 1. The drill bit 40 may have a proximal coupling end 410, a distal drilling end 420 and a central cylindrical shaft portion 430 disposed therebetween. A set of calibration marks 440 may be provided along at least a portion of the shaft 430. These calibration marks may be used to determine the depth to which the drill has been driven into bone. Thus, when the drill bit 40 is inserted into the drill sleeve 20 as shown in FIG. 9, the user may read the calibration mark 440 located directly adjacent the drill sleeve flange proximal face 214 to determine the distance beyond the distal end 220 of the drill sleeve 20 that the distal cutting end 420 of the drill 40 has been extended. This arrangement thus allows a quick and easy manner of determining drilling depth.

Figure 8:
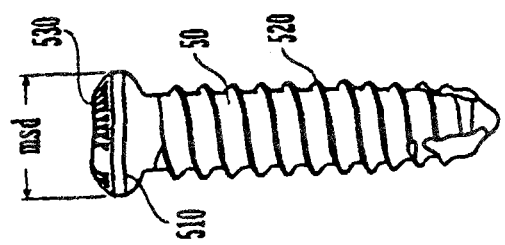
FIG. 8 is a side view of an exemplary bone screw for use with the device of FIG. 1.

FIG. 8 shows an exemplary fastener for use with the device 1 in which bone screw 50 has a head 510 and a threaded shank 520, the head having a maximum diameter "msd" that is slightly smaller than the inner diameter "pid" of protection sleeve 30. The head may further have a drive recess 530 configured to receive the driving tip 610 of screwdriver 60 (see FIG. 10) to drive the bone screw 50 into bone. Thus, as illustrated in FIG. 3, protection sleeve 30 is sized to receive bone screw 50 and screwdriver 60 to allow the screw 50 to be driven into the underlying bone via protection sleeve 30 and along axis "C-C."

A method of using the invention to engage a bone fastener with a fixation device and underlying bone is also provided. To assemble the device 1, drill sleeve 20 may be inserted into protection sleeve 30 until the circumferential ridge 2000 of the drill sleeve engages the proximal end 310 of the protection sleeve. Thereafter, the application of force against the drill sleeve 20, while holding the protection sleeve 30 steady, may cause the proximal end 210 of the drill sleeve to compress along slots 2050, 2060 allowing the circumferential ridge 2000 to pass into engagement with recess 3000 in the protection sleeve 30. Once the ridge 2000 and recess 3000 are engaged, the sleeves 20, 30 are provisionally axially locked together. The trocar 10 may then be inserted into the drill sleeve 20.

The assembled device 1 (FIG. 1) may then be inserted into an incision in the patient overlying a targeted bone screw hole of a fixation element. The user may insert the pointed end 3 of the device 1 into the incision, pressing the device down through the tissue by applying force to the device flanges 112, 212, 312. The tapered distal end surfaces 122, 220, 320 may serve to separate the tissue, facilitating passage of the device therethrough. Once the distal end 3 of the device 1 contacts the bone, the trocar 10 may be removed, and a drill bit may be 40 inserted through the bore 236 of the drill sleeve. The drill bit 40 may be advanced until the cutting end engages bone, and drilling may be performed until a desired depth is reached, as indicated by calibration marks 440 on the drill bit. The drill bit 40 may be removed from the drill sleeve 20, and drill sleeve 20 may be removed from the protection sleeve by squeezing together the arms 2110, 2120 of the proximal flange 212 and pulling the drill sleeve 20 up and away from the protection sleeve 30. An appropriately sized bone screw 50 may then be engaged with the end of a screwdriver 60 and the two may be inserted into the bore 336 of the protection sleeve 30 via the sleeve proximal end 310. The screw 50, and screwdriver 60 may then be advanced through the sleeve to engage the fixation device and/or the drilled hole in the bone. The screwdriver 60 may then be used to drive the bone screw into the bone hole, fixing the fixation device to the bone. Thereafter, the screwdriver 60 and protection sleeve 30 may be removed from the incision and the incision may be sutured closed.

Figures 11A, 11B, 11C:
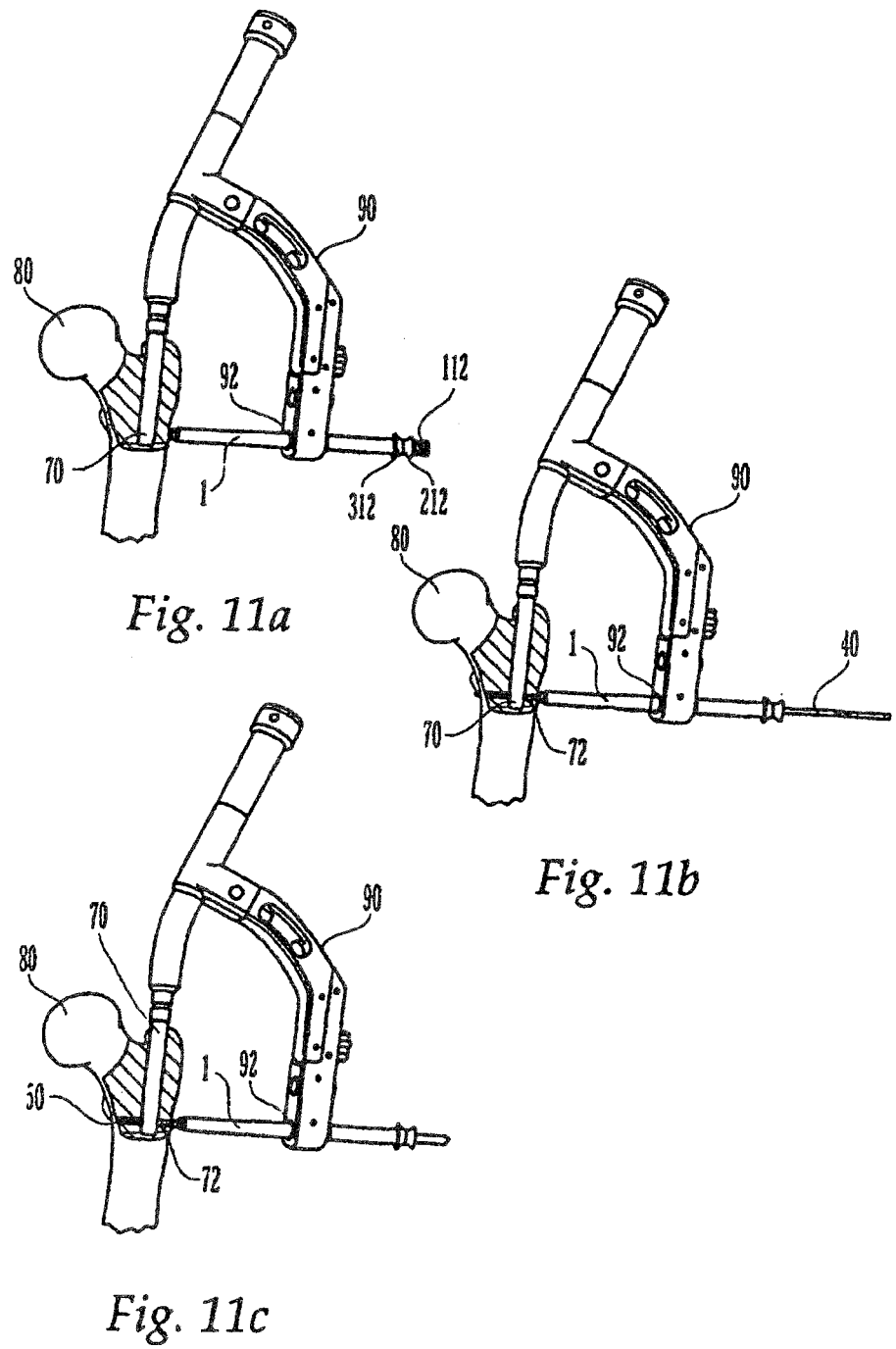
FIGS. 11a through 11c are perspective views of the device of FIG. 1 being used with an aiming arm of an intramedullary nail assembly inserted in a femur.

FIGS. 11a-11c illustrate the use of the invention for installing locking screws in the shaft of an intramedullary nail. As illustrated, intramedullary nail 70 is inserted in the intramedullary canal of a patient femur 80. Aiming arm 90 is engaged with the nail 70, and is used to guide the trajectory of the locking screw 50 to precisely align with one or more pre-formed fixation holes 72 in the nail 70. Further description of the aiming arm and associated instruments is provided in co-pending non-provisional U.S. patent application Ser. No. 09/978,002 to Roth filed Oct. 17, 2001 and titled "Bone Fixation Systems," the entirety of which application is incorporated herein by reference.

Thus, the device 1 may be inserted into an appropriate bore 92 in the aiming arm 90 corresponding to a fixation hole 72 in the nail 70. The outer surface 332 of the protection sleeve 30 may slide within the aiming arm bore 92 to align the device 1 with the fixation hole 72. An incision may be made in the skin over the insertion point for the device 1, and by applying a force to the device flanges 112, 212, 312, the device may be driven through the incision and into alignment with the targeted fastener hole. The trocar 10 may be removed, and drilling and screw insertion functions may be performed as previously described.

Figure 12A:
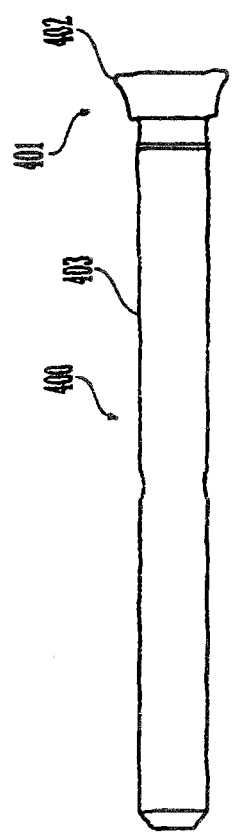
FIGS. 12a and 12b are side and cross section views of a wire guide sleeve for use with the protection sleeve of FIGS. 4a-c.
Figure 12B:
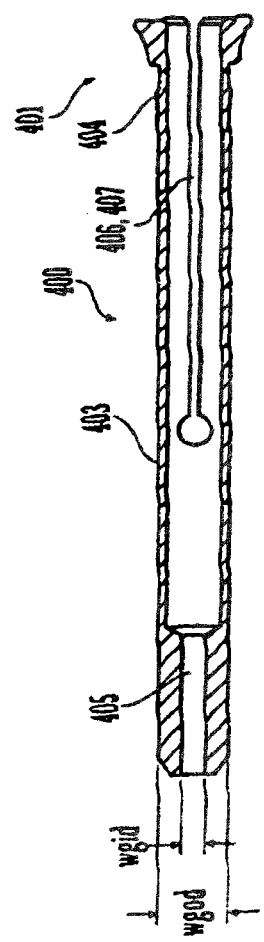
Figure 13:
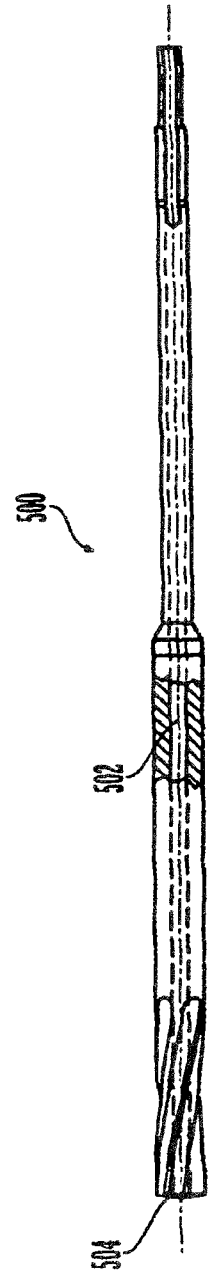
FIG. 13 is a partial cross section view of a drill used with the protection sleeve of FIGS. 4a-c.
Figure 14:
FIG. 14 is a side view of a guide wire for use with the protection sleeve of FIGS. 4a-c and the wire guide sleeve of FIGS. 12a-b.

Shown in FIGS. 12a & b is a wire guide sleeve 400 that may be used together with the protection sleeve 30 of FIGS. 4a-c to create an initial opening in bone for insertion of an intramedullary nail. Alternatively, the sleeves 400, 30 may be used for inserting a spiral blade or helical blade into a fractured femoral head to connect the head to the associated femoral shaft. A large pre-drilled bone hole may be required to receive such large fixation devices (e.g. from about 8 mm to about 17 mm), and thus the protection sleeve may be used for receiving and guiding the large sized drill bit 500 (see FIG. 13) for drilling the hole in the bone. The wire guide sleeve 400 may be used for engaging a guide wire 600 (see FIG. 14) for aligning the sleeves 400, 30 with the bone segments to be fixed. The guide wire 600 may be pre-inserted in at least one bone segment to provide precise alignment of the sleeves 400, 30 to ensure the drilled bone hole will have the precise trajectory desired by the surgeon. A bone hole thus prepared may ensure that the installed fixation device engages the bone portions in a manner that will best facilitate fusion of the fractured bone segments.

The wire guide sleeve 400 may have any or all of the features of the drill sleeve 20 described in relation to FIGS. 3a-e (e.g. tapered distal end 401, proximal flange element 402, generally cylindrical body portion 403, color coding, etc.). The wire guide sleeve 400 may also comprise any of the locking features as described in relation to FIGS. 3a-e for provisionally axially locking the wire guide sleeve 400 to the protection sleeve 30. In the illustrated embodiment, the wire guide sleeve 400 has a circumferential ridge 404 having all of the features described in relation to circumferential ridge 2000 of drill sleeve 20 (see FIG. 3c), and also has longitudinal slots 406, 407 having all the features described in relation to slots 2050, 2060 of the drill sleeve 20 (see FIG. 3a). Further, the wire guide sleeve 400 may have a distal inner surface portion 405 sized and configured to coaxially receive the guide wire 600. In the illustrated embodiment, the distal inner surface portion may have an inner diameter "wgid" of about 3.3 mm, which may accept a standard 3.0 mm guide wire. The outer surface diameter "wgod" of the wire guide sleeve 400 may be from about 4 mm to about 17 mm, to allow it to be slidably received within the longitudinal bore 336 of the protection sleeve 30. Thus, the wire guide sleeve 400 may be received within the protection sleeve 30 and the assembled sleeves may thus receive the guide wire 600. It is noted that the indicated dimensions are provided for purposes of illustration only, and that other sizes, both larger and smaller, are also contemplated.

To use the combination of the protection sleeve 30/wire guide sleeve 400 for forming an opening in a femur into which an intramedullary nail may be inserted, the surgeon may first make an incision in the patient's skin to the depth of the bone. The protection sleeve 30, guide sleeve 400 and trocar 10 may be nested together as previously described in relation to FIG. 1 and driven through the incision down to the bone. The trocar 10 may then be removed and a guide wire inserted through the cannulation 405 in the wire guide sleeve 400 and advanced into the bone under x-ray or fluoroscopic observation. The guide wire 600 may have a threaded or drilling tip 602 that may allow the surgeon to positively engage the guide wire 600 to the bone. Once the guide wire is properly positioned, the wire guide sleeve 400 may then be disengaged from the protection sleeve 30 by radially compressing the flange 402 to disengage the locking feature, and may be slipped off the free end 604 of the guide wire 600. A drill 500 having a cannulation 502 may be placed over the free end 604 of the guide wire 14 and inserted into the bore 336 of the protection sleeve 30. The drill 500 may be advanced through the protection sleeve 30 until the tip 504 contacts bone and then may be rotated to drill the desired hole in the bone. Once the bone hole has been formed, the drill 500 and protection sleeve 30 may then be removed from the incision. The guide wire 600 may be removed or it may be left in place to be used as part of a subsequent procedure.

To use the combination of the protection sleeve 30/wire guide sleeve 400 for installing a helical blade, the surgeon may undertake the same steps as described above, with the exception that instead of removing the protection sleeve 30 and guide wire 600 after the hole has been drilled, the surgeon may retain both elements in place and remove only the drill bit 500. Thereafter, a cannulated helical blade or spiral blade may be slipped over the free end 604 of the guide wire and inserted into the bore 336 of the protection sleeve 30. A cannulated driving tool may follow the helical or spiral blade over the guide wire 600 and may be used to drive the blade into to the hole in the bone.

The protection sleeve 30, drill sleeve 20, wire guide sleeve 400, trocar 10 and any or all of the other described instruments may be provided as part of an orthopedic kit for use during surgical procedures in which percutaneous placement of fasteners will be performed. Thus, the kit may comprise one or more device, and each device may comprise a trocar, drill sleeve, and protection sleeve sized to correspond to a different screw size. Likewise, if the kit includes a wire guide sleeve 400, it as well as the trocar and protection sleeve may be sized to correspond to different nail or spiral/helical blade sizes.

In an exemplary embodiment for use with an intramedullary nail, the kit may contain three separate devices sized to correspond to screw sizes of 3.2 mm, 4.0 mm and 5.0 mm, respectively. Other device sizes may be provided as desired.

The trocar 10, drill sleeve 20, wire guide sleeve 400 and protection sleeve 30 may be made of stainless steel, titanium, polymer or any other appropriate material. In one embodiment, the trocar, drill sleeve and protection sleeve are manufactured from a martinsitic stainless steel.

The trocar 10, drill sleeve 20, wire guide sleeve 400 and protection sleeve 30 also may be manufactured from a radiolucent or partially radiolucent materials such as ultra high molecular weight polyethylene (UHMWPE), polyether-ether-ketone (PEEK), extruded carbon fiber or other such material. Any or all of the components of the system may also be disposable.

It will be appreciated that although the invention has been described in relation to its use with an intramedullary nail system, that the invention may be applied to any orthopedic application in which a stabilizing device, such as a bone plate, rod, nail, etc., is to be applied to a bone. Thus, the invention may find application in maxillofacial indications where small-sized plates are applied to portions of the cranio-facial skeleton and where screw sizes may be as small as 1.0 mm. Likewise, the invention may be used in large-scale applications, accepting up to 17 mm drills used for installation of spiral blades, helical blades, or for facilitating opening the insertion site for an intramedullary nail.

What is claimed:

1. An orthopedic system, comprising:
 a protection sleeve having proximal and distal ends, a longitudinal axis and first inner and outer surfaces, the protection sleeve further having a protrusion extending inward from the first inner surface into a first longitudinal bore extending therethrough; and
 a drill sleeve having proximal and distal ends, a longitudinal axis, second inner and outer surfaces and a second longitudinal bore extending therethrough, the second outer surface configured to be received within at least a portion of the protection sleeve, the drill sleeve having a recess extending into the second outer surface, the protrusion and recess cooperating to releasably axially lock the protection sleeve with the drill sleeve, the sleeves being separable from each other by applying an axial separation force between the protection and drill sleeves and a radial compression force to at least a portion of the drill sleeve,
 wherein the inner surface of at least one of the protection and drill sleeves is configured to receive a drill bit for drilling a hole in bone.

2. The system of claim 1, further comprising:
 a trocar configured for insertion through the second longitudinal bore.

3. The system of claim 1, further comprising:
 a first flange located on the proximal end of the drill sleeve and a first tapered tip on the distal end of the drill sleeve; and
 a second flange located on the proximal end of the protection sleeve and a second tapered tip on the distal end of the protection sleeve.

4. The system of claim 3, wherein the first longitudinal bore is configured to receive a driver and bone fastener therethrough to allow insertion of the fastener into bone in a direction along the longitudinal axis thereof.

5. The system of claim 4, wherein at least one of the first and second tapered tips is configured to align with a fastener hole in a bone fixation element.

6. The system of claim 5, wherein the bone fixation element is one of a bone plate and an intramedullary nail.

7. The system of claim 1, wherein the protrusion comprises a plurality of discrete protruding elements.

8. The system of claim 1, wherein the protrusion comprises at least one circumferential ridge.

9. The system of claim 8, wherein the recess comprises at least one circumferential groove corresponding to the at least one circumferential ridge.

10. The system of claim 9, wherein the protrusion comprises first and second tapered surfaces.

11. The system of claim 9, wherein the drill sleeve comprises at least one longitudinal slot extending between the second inner and outer surfaces, the slot running from at least one end of the drill sleeve and having a length, the slot further configured to render at least a portion of the drill sleeve radially flexible.

12. The system of claim 11, wherein the at least one slot divides a first end of the drill sleeve into first and second halves, wherein pressing the first and second halves toward each other disengages the ridge from the recess, thereby allowing the protection and drill sleeves to be axially locked with, or separated from, each other.

13. The system of claim 11, wherein the drill sleeve has two longitudinal slots diametrically disposed with respect to each other about the circumference of the drill sleeve.

14. The system of claim 8, wherein the protrusion comprises at least one tapered surface configured to facilitate radial compression of the drill sleeve when the drill sleeve is inserted into the first longitudinal bore.

15. The system of claim 2, wherein the protection sleeve, drill sleeve and the trocar are color coded to provide a visual indication of the size of a bone screw that can be received through the first longitudinal bore.

16. The system of claim 1, wherein the outer surface of the protection sleeve is configured to be received within the bore of an aiming arm of an intramedullary nail to align the protection sleeve with a targeted fastener hole in a portion of the intramedullary nail.

* * * * *